United States Patent

Oppenheim et al.

Patent Number: 5,631,228
Date of Patent: May 20, 1997

[54] ANTI-FUNGAL AND ANTI-BACTERIAL HISTATIN-BASED PEPTIDES

[75] Inventors: Frank G. Oppenheim, Chestnut Hill; Tao Xu, Newton; F. Donald Roberts, Dover, all of Mass.

[73] Assignees: Periodontix, Inc., Del.; The Trustees of Boston University, Mass.

[21] Appl. No.: 481,888

[22] Filed: Jun. 7, 1995

Related U.S. Application Data

[63] Continuation-in-part of Ser. No. 287,717, Aug. 9, 1994, Pat. No. 5,486,503, which is a continuation of Ser. No. 145,030, Oct. 28, 1993, abandoned, which is a continuation of Ser. No. 786,571, Nov. 1, 1991, abandoned.

[51] Int. Cl.$^6$ .......................... A61K 38/08; A61K 38/10; C07K 7/06; C07K 7/08
[52] U.S. Cl. .................... 514/12; 514/12; 514/13; 514/14; 514/15; 530/324; 530/325; 530/326; 530/327; 435/64.1; 435/257.3; 435/320.1
[58] Field of Search ................ 435/252.3, 320.1, 435/69.1; 514/2, 12–15; 530/324, 325, 326, 327

[56] References Cited

U.S. PATENT DOCUMENTS

| | | | |
|---|---|---|---|
| 4,725,576 | 2/1988 | Pollock et al. | 514/2 |
| 5,032,574 | 7/1991 | Wilde et al. | 514/12 |
| 5,221,732 | 6/1993 | Chen et al. | 530/326 |
| 5,225,399 | 7/1993 | Zasloff et al. | 514/13 |
| 5,239,059 | 8/1993 | Zasloff et al. | 530/325 |
| 5,304,633 | 4/1994 | Tomita et al. | 530/327 |
| 5,324,716 | 6/1994 | Selsted et al. | 514/14 |
| 5,486,503 | 1/1996 | Oppenheim et al. | 514/2 |

FOREIGN PATENT DOCUMENTS

| | | |
|---|---|---|
| 6-234653 | 8/1994 | Japan. |
| 6-287146 | 10/1994 | Japan. |

OTHER PUBLICATIONS

Edgerton, M., et al., Journal of Biomedical Material Research, vol. 29, "Surface-modified poly(methyl methacrylate) enhances adsorption and retains anticandidal activities of salivary histatin 5", pp. 1277–1286, 1995.

Zuo, Y., et al., Gene, vol. 161, "Recombinant histatins: functional domain duplication enhances candidacidal activity", pp. 87–91, 1995.

Murakami, Y. et. al., "Inhibitory Effects of Synthetic Histidine–Rich Peptides on Haemagglutination by Bacteroides Gingivalis 381", *Arch. Oral Biol.*, 35(9): 775–777 (1990).

Oppenheim, F.G. et. al., "Histatins, a Novel Family of Histidine–Rich Proteins in Human Paretoid Secretion", *J. Biol. Chem.*, 263(16):7472–7477 (Jun. 1988).

Xu, T. et. al., "Anticandidal Activity of Major Human Salivary Histatins", *Infect. Immunol.*, 59(8):2549–2554 (Aug. 1991).

Xu, T. et al., "Anti–fungal Functional Domain of Histatin 3", *J. Dent. Res.* 70:497 (Apr. 1991) (Abstract No. 1852).

Raj, P.A. et al., "Salivary Histatin 5: Depnedence of Sequence, Chain Length, and Helical Confirmation for Candidacidal Activity", *J. Biol. Chem.*, 265(7):3898–3905 (Mar. 15, 1990).

Santarpia III, R.P. et. al., "A Comparison of the Inhibition of Blastospore Viability and Germ–Tube Development in *Candida albicans* by Histidine Peptides and Ketoconazole", *Arch. Oral Biol.*, 33(8):567–573 (1988).

Santarpia III, R.P. et. al., "Preliminary Findings for In Vivo Efficacy of Salivary Histidine–Rich Polypeptides", *J. Dent. Res.*, 69:173 (Mar. 1990).

Troxler, R.F. et. al., "Structural Relationship Between Human Salivary Histatins", *J. Dent. Res.*, 69(1):2–6 (Jan. 1990).

Xu, T. et al., "Primary Structure and Anticandidal Activity of the Major Histatin from Parotid Secretion of the Subhuman Primate, *Macac fascicularis,*" *J. Dent. Res.*, 69(11):1717–1723 (Nov. 1990).

Xu, T. et al., "Structure/Function Analysis of Anti–Candida Activities of Histatin 1," *J. Dent. Res.*, 68:973 (Jun. 1989).

Nishikata, M. et al., "Salivary Histatin as an Inhibitor of a Protease Produced by the Oral Bacterium *Bacteroides gingivalis,*" *Biochem. Biophys. Res. Comm.*, 174(2):625–630 (Jan. 31, 1991).

*Primary Examiner*—Robert A. Wax

*Assistant Examiner*—William W. Moore
*Attorney, Agent, or Firm*—Hamilton, Brook, Smith & Reynolds, P.C.

[57]  ABSTRACT

Histatin-based peptides representing defined portions of the amino acid sequences of naturally occurring human histatins and methods for treatment of fungal or bacterial infection are described. These histatin-based peptides represent the active anti-fungal and anti-bacterial region of naturally occurring human histatins.

8 Claims, 6 Drawing Sheets

```
Histatin 1:  Asp-Pse-His-Glu-Lys-Arg-His-His-Gly-Tyr-Arg-Arg-Lys-Phe-His-Glu-Lys-His-His-
                1                  5                     10                    15
Histatin 2:                                               Arg-Lys-Phe-His-Glu-Lys-His-His-
Histatin 3:  Asp-Ser-His-Ala-Lys-Arg-His-His-Gly-Tyr-Lys-Arg-Lys-Phe-His-Glu-Lys-His-His-
                1                  5                     10                    15
Histatin 4:                                           Arg-Lys-Phe-His-Glu-Lys-His-His-
Histatin 5:  Asp-Ser-His-Ala-Lys-Arg-His-His-Gly-Tyr-Lys-Arg-Lys-Phe-His-Glu-Lys-His-His-
Histatin 6:  Asp-Ser-His-Ala-Lys-Arg-His-His-Gly-Tyr-Lys-Arg-Lys-Phe-His-Glu-Lys-His-His-
Histatin 7:                                           Arg-Lys-Phe-His-Glu-Lys-His-His-
Histatin 8:                                               Lys-Phe-His-Glu-Lys-His-His-
Histatin 9:                                           Arg-Lys-Phe-His-Glu-Lys-His-His-
Histatin 10:                                              Lys-Phe-His-Glu-Lys-His-His-
Histatin 11: Lys-Arg-His-His-Gly-Tyr-Lys-Arg
Histatin 12: Lys-Arg-His-His-Gly-Tyr-Lys
Peptide 101: Lys-Arg-His-His-Gly-Tyr-Lys-Arg-Lys-Phe-His-Glu-Lys-His-His-
Peptide 102:              Gly-Tyr-Lys-Arg-Lys-Phe-His-Glu-Lys-His-His-
Peptide 103: Lys-Arg-His-His-Gly-Tyr-Lys-Arg-Lys-Phe-His-Glu-Lys-His-His-
```

FIGURE 1A

```
                    10              15
Peptide 104:       Gly-Tyr-Lys-Arg-Lys-Phe-His-Glu-Lys-His-His-
Peptide 105:  Lys-Arg-His-His-Gly-Tyr-Lys-Arg-Lys-Phe-His-Glu-Lys-Phe-His
Peptide 113:  Ala-Lys-Arg-His-His-Gly-Tyr-Lys-Arg-Lys-Phe-His-Glu-Lys-Phe-His
Peptide 117:  Lys-Arg-His-His-Gly-Tyr-Lys-Arg-Lys-Phe-His
Peptide 118:  Ala-Lys-Arg-His-His-Gly-Tyr-Lys-Arg-Lys-Phe
Peptide 119:  Ala-Lys-Arg-His-His-Gly-Tyr-Lys-Arg-Lys
Peptide 120:  Ala-Lys-Arg-His-His-Gly-Tyr-Lys-Arg
Peptide 129:  Lys-Arg-His-His-Gly-Tyr-Lys-Arg-Lys-Phe 20              25              30              35
Histatin 1:   Ser-His-Arg-Glu-Phe-Pro-Phe-Tyr-Gly-Asp-Tyr-Gly-Ser-Asn-Tyr-Leu-Tyr-Asp-Asn
Histatin 2:   Ser-His-Arg-Glu-Phe-Pro-Phe-Tyr-Gly-Asp-Tyr-Gly-Ser-Asn-Tyr-Leu-Tyr-Asp-Asn
Histatin 3:   Ser-His-Arg-Gly-Tyr-Arg-Ser-Asn-Tyr-Leu-Tyr-Asp-Asn
Histatin 4:   Ser-His-Arg-Gly-Tyr-Arg-Ser-Asn-Tyr-Leu-Tyr-Asp-Asn
Histatin 5:   Ser-His-Arg-Gly-Tyr
Histatin 6:   Ser-His-Arg-Gly-Tyr-Arg
Histatin 7:   Ser-His-Arg-Gly-Tyr
```

FIGURE 1B

```
                    20                    25
Histatin 8:    Ser-His-Arg-Gly-Tyr
Histatin 9:    Ser-His-Arg-Gly-Tyr-Arg
Histatin 10:   Ser-His-Arg-Gly-Tyr-Arg
Peptide 101:   Ser-His-Arg-Gly-Tyr-Arg
Peptide 102:   Ser-His-Arg-Gly-Tyr-Arg
Peptide 103:   Ser-His-Arg
Peptide 104:   Ser-His-Arg
```

FIGURE 1C

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /product= "PSE"

( x i ) SEQUENCE DESCRIPTION: SEQ ID NO:1:

```
Asp  Xaa  His  Glu  Lys  Arg  His  His  Gly  Tyr  Arg  Arg  Lys  Phe  His  Glu
 1              5                        10                       15

Lys  His  His  Ser  His  Arg  Glu  Phe  Pro  Phe  Tyr  Gly  Asp  Tyr  Gly  Ser
                20                       25                       30

Asn  Tyr  Leu  Tyr  Asp  Asn
                35
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

```
Arg  Lys  Phe  His  Glu  Lys  His  His  Ser  His  Arg  Glu  Phe  Pro  Phe  Tyr
 1              5                        10                       15

Gly  Asp  Tyr  Gly  Ser  Asn  Tyr  Leu  Tyr  Asp  Asn
                20                       25
```

( 2 ) INFORMATION FOR SEQ ID NO:3:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

```
Asp  Ser  His  Ala  Lys  Arg  His  His  Gly  Tyr  Lys  Arg  Lys  Phe  His  Glu
 1              5                        10                       15

Lys  His  His  Ser  His  Arg  Gly  Tyr  Arg  Ser  Asn  Tyr  Leu  Tyr  Asp  Asn
                20                       25                       30
```

( 2 ) INFORMATION FOR SEQ ID NO:4:

( i ) SEQUENCE CHARACTERISTICS:
        ( A ) LENGTH: 21 amino acids
        ( B ) TYPE: amino acid (C) STRANDEDNESS:
            (D) TOPOLOGY: linear (ii) MOLECULE TYPE: peptide (xi) SEQUENCE DESCRIPTION: SEQ ID NO:4:

Arg  Lys  Phe  His  Glu  Lys  His  His  Ser  His  Arg  Gly  Tyr  Arg  Ser  Asn
    1                   5                        10                         15

Tyr  Leu  Tyr  Asp  Asn
                   20

(2) INFORMATION FOR SEQ ID NO:5:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Asp  Ser  His  Ala  Lys  Arg  His  His  Gly  Tyr  Lys  Arg  Lys  Phe  His  Glu
    1                   5                        10                         15

Lys  His  His  Ser  His  Arg  Gly  Tyr
                   20

(2) INFORMATION FOR SEQ ID NO:6:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Asp  Ser  His  Ala  Lys  Arg  His  His  Gly  Tyr  Lys  Arg  Lys  Phe  His  Glu
    1                   5                        10                         15

Lys  His  His  Ser  His  Arg  Gly  Tyr  Arg
                   20                     25

(2) INFORMATION FOR SEQ ID NO:7:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Arg  Lys  Phe  His  Glu  Lys  His  His  Ser  His  Arg  Gly  Tyr
    1                   5                        10

(2) INFORMATION FOR SEQ ID NO:8:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

```
Lys Phe His Glu Lys His His Ser His Arg Gly Tyr
1               5                   10
```

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

```
Arg Lys Phe His Glu Lys His His Ser His Arg Gly Tyr Arg
1               5                   10
```

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( x i ) SEQUENCE DESCRIPTION: SEQ ID NO:10:

```
Lys Phe His Glu Lys His His Ser His Arg Gly Tyr Arg
1               5                   10
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

```
Lys Arg His His Gly Tyr Lys Arg
1               5
```

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

```
Lys Arg His His Gly Tyr Lys
1               5
```

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

```
Lys Arg His His Gly Tyr Lys Arg Lys Phe His Glu Lys His His Ser
1               5                   10                  15
```

His Arg Gly Tyr Arg
                20

( 2 ) INFORMATION FOR SEQ ID NO:14:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

Gly Tyr Lys Arg Lys Phe His Glu Lys His His Ser His Arg Gly Tyr
1               5                   10                  15
Arg ( 2 ) INFORMATION FOR SEQ ID NO:15:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

Lys Arg His His Gly Tyr Lys Arg Lys Phe His Glu Lys His His Ser
1               5                   10                  15
His Arg ( 2 ) INFORMATION FOR SEQ ID NO:16:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:16:

Gly Tyr Lys Arg Lys Phe His Glu Lys His His Ser His Arg
1               5                   10

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:17:

Lys Arg His His Gly Tyr Lys Arg Lys Phe His Glu Lys His His
1               5                   10                  15

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:18:

Ala Lys Arg His His Gly Tyr Lys Arg Lys Phe His
1               5                   10

( 2 ) INFORMATION FOR SEQ ID NO:19:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:19:

Lys Arg His His Gly Tyr Lys Arg Lys Phe His
1               5                   10

( 2 ) INFORMATION FOR SEQ ID NO:20:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:20:

Ala Lys Arg His His Gly Tyr Lys Arg Lys Phe
1               5                   10

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:21:

Ala Lys Arg His His Gly Tyr Lys Arg Lys
1               5                   10

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:22:

Ala Lys Arg His His Gly Tyr Lys Arg
1               5

( 2 ) INFORMATION FOR SEQ ID NO:23:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:23:

| Lys | Arg | His | His | Gly | Tyr | Lys | Arg | Lys | Phe |
|---|---|---|---|---|---|---|---|---|---|
| 1 | | | | 5 | | | | | 10 |

ANTI-FUNGAL AND ANTI-BACTERIAL HISTATIN-BASED PEPTIDES

GOVERNMENT SUPPORT

The invention described herein was supported in whole or in part by Grant No. DE07652 from the National Institutes of Health, which have certain rights in the invention.

RELATED APPLICATIONS

This is a Continuation-in-Part of U.S. patent application Ser. No. 08/287,717, filed Aug. 9, 1994, now U.S. Pat. No. 5,486,503 which is a File Wrapper Continuation of U.S. patent application Ser. No. 08/145,030, filed Oct. 28, 1993 (now abandoned), which is a File Wrapper Continuation of U.S. patent application Ser. No. 07/786,571, filed Nov. 1, 1991 (now abandoned), the contents of which are incorporated herein by reference in their entirety.

BACKGROUND OF THE INVENTION

The family of naturally occurring human histatins is a group of twelve low molecular weight, abundant in histidine, peptides found in human submandibular and parotid salivary secretions (Oppenheim et al. (1986), *J. Biol. Chem.* 261:1177–1182; Oppenheim et al. (1988), *J. Biol. Chem.* 263:7472–7477; Troxler et al. (1990), *J. Dent. Res.* 69:2–6). The primary structure of the major family members (histatins 1, 3, and 5; 70–80% of the whole family) has shown that these proteins consist of 38, 32 and 24 amino acid residues, respectively. There is a high degree of homology among these three major histatins. Histatin 5 results from post-translational cleavage of histatin 3. Many of the smaller members of the histatin family may also, in fact, originate by post-translational proteolysis of histatins 1, 3 and 5 (Oppenheim et al. (1989), *Human Saliva: Clinical Chemistry and Microbiology Vol.* 1 CRC Press, Boca Raton, Fla., ed. Tenovuo, J. O.; Lal et al. (1992), *Arch. Oral Biol.* 37:7–13). The genes that encode histatins 1 and 3 have been localized chromosomally (vanderSpek et al., (1989), *Am. J. Hum. Genet.* 45:381–387) and sequenced (Sabatini, L. M. et al. (1989), *Biochem. Biophys. Res. Comm.* 160:495–502). Histatins 1 and 3 appear to be derived from separate genes.

The three major human histatins exhibit specific antimicrobial activities towards diverse oral microbiota. These histatins, at physiological concentrations, are capable of killing *Candida albicans* in both blastopore and mycelial forms (Pollock, J. J. et al. (1984), *Infect. Immun.* 44:702–707; Xu, T. et al. (1991), *Infect. Immun.* 59(8): 2549–2554). Histatins are also capable of killing oral bacteria, including *Streptococcus mutans* (MacKay, B. J. et al. (1984), *Infect. Immun.* 44:695–701; Xu, T. et al. (1990), *J. Dent. Res.* 99:239), *Porphyromonas gingivalis* (Colon et al. (1993), *J. Dent. Res.* 72:322) and *Actinomyces viscosus* (Kalpidis et al. (1992) *J. Dent. Res.* 72:305).

Infection with the yeast *Candida albicans* is a prevalent and, in some cases, life-threatening condition affecting otherwise healthy and immuno-compromised patients. Candidal vaginitis is estimated to affect 15 to 55% of healthy young women. Candidal infections often occur in diabetics, during pregnancy, and following medication with antibiotics, steroid hormones, or oral contraceptives. (Tapper-Jones, L. M. et al. (1981) *J. Clin. Pathol.* 34:706–11; Sobel, J. D. et al. (1984) *Infect. Immun.* 44:576–580). Oral candidiasis is an early opportunistic infection of Acquired Immune Deficiency Syndrome (AIDS) in individuals infected with human immunodeficiency virus type 1, as well as a complication of radiation and chemotherapy in cancer patients. (Yeh, C.-K. et al. (1988) *J. of Acquired Immune Deficiency Syndromes* 1:361–366). In addition, candidal infection of denture wearers plays a primary role in dental stomatitis, a prevalent oral problem among the elderly. (Pollock, J. J. et al. (1990) *NYS Dental J.* 56:36–38). Candidal infections of skin and urethra are widespread problems. In patients in intensive care and immuno-compromised patients, systemic fungal infection often leads to death, since there are few safe and effective anti-fungal pharmaceuticals for intravenous use. (Burnie, J. P. et al. (1985) *British Medical Journal* 290:746–748). Similarly, infections with various bacterial species can cause severe disease states and even death.

Although several anti-fungal agents (e.g., clotrimazole, miconazole, ketoconazole, and nystatin) and anti-bacterial agents (penicillin, streptomycin, tetracycline and chlorhexidine) are currently available, these agents are not completely effective, can lead to drug resistant organisms and can produce adverse side effects. Many are not appropriate for oral or systemic administration. Thus, a potent, naturally occurring anti-fungal or anti-bacterial substance would provide a significant improvement in the treatment of microbial infection.

SUMMARY OF THE INVENTION

This invention is based on substantially pure peptides which have anti-candidal or anti-bacterial activity which are equivalent to that of naturally occurring histatins but are smaller in size. These peptides represent defined portions of the amino acid sequences of naturally occurring human histidine-rich salivary proteins called histatins, and will be referred to herein as histatin-based peptides. As demonstrated herein, these histatin-based peptides have been shown to be superior, particularly on a weight basis, in anti-candidal or anti-bacterial activity over the naturally occurring histatins. Thus, this invention provides compositions for treatment of fungal or bacterial infection comprising histatin-based peptides with defined amino acid sequences. These peptides are derived from a specific histatin-based peptide having a specified 12 amino acid sequence. This peptide is designated as peptide 113 (SEQ ID NO: 18). Other peptides with significant anti-fungal or anti-bacterial activities have sequence portions of at least 8 amino acids from this histatin-based peptide.

BRIEF DESCRIPTION OF FIGURES

FIGS. 1A–1C shows the amino acid sequences of human histatins and peptides 101, 102, 103, 104, 105, 113, 117, 118, 119, 120 and 129.

DETAILED DESCRIPTION OF THE INVENTION

Figure 2:
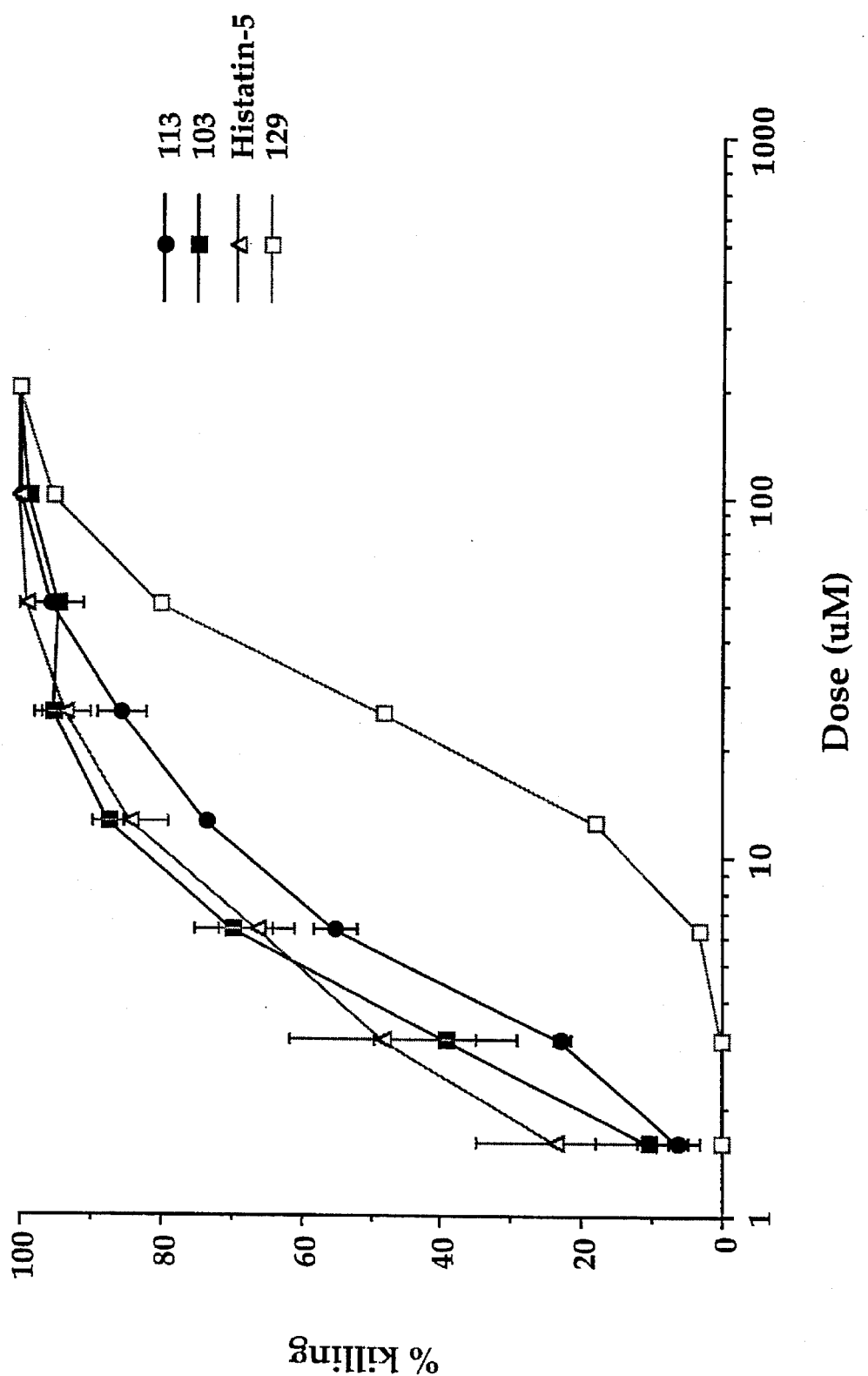
FIG. 2 is a graph that shows the % killing of *C. albicans* blastoconidia as a function of the concentration of histatin-5, peptide 103, peptide 113 and peptide 129.

This invention relates to peptides which have anti-fungal or anti-bacterial activity, in which the amino acid sequences represent defined portions of the amino acid sequences of naturally occurring human histidine-rich salivary proteins called histatins. (Histatins are also referred to in the literature as histidine-rich proteins or HRPs.) Histatins are major salivary proteins which are synthesized in the parotid and submandibular-sublingual secretory glands of humans and Old World monkeys. (Azen, E. A. (1978) *Biochem. Genet.* 16:79–99). Histatins are believed to be part of an extraimmunologic defense system of the oral cavity. The anti-fungal activity of histatins, as well as their inhibitory effect on several oral bacteria (such as the cariogenic *Streptococcus mutans* and the periodontal pathogen *Porphyromonas gingivalis*), have been demonstrated in vitro. In addition, the observation that polyhistidine peptides inactivate herpes simplex virus in vitro and that whole saliva contains inhibitors of human immunodeficiency virus suggests the possibility that histatins may have anti-viral activity. These in vitro studies support potential clinical use of compositions containing histatins or histatin-based peptides for the treatment of local and systemic candidal infection, oral bacterial diseases, such as caries and periodontitis, systemic bacterial infection and viral infection. Vaginal, urethral, skin, oral or ophthalmic fungal or bacterial infections are particularly susceptible to histatin-based peptide therapy. Microbes which are specifically amenable to histatin-based peptide therapy are:

a) *Candida albicans;*
b) *Actinomyces actinomycetemcomitans;*
c) *Actinomyces viscosus;*
d) *Bacteroides forsythus;*
e) *Bacteriodes fragilis;*
f) *Bacteriodes gracilis;*
g) *Bacteriodes ureolyticus;*
h) *Campylobacter concisus;*
i) *Campylobacter rectus;*
j) *Campylobacter showae;*
k) *Campylobacter sputorum;*
l) *Capnocytophaga gingivalis;*
m) *Capnocytophaga ochracea;*
n) *Capnocytophaga sputigena;*
o) *Clostridium histolyticum;*
p) *Eikenella corrodens;*
q) *Eubacterium nodatum;*
r) *Fusobacterium nucleatum;*
s) *Fusobacterium periodonticum;*
t) *Peptostreptococcus micros;*
u) *Porphyromonas endodontalis;*
v) *Porphyromonas gingivalis;*
w) *Prevotella intermedia;*
x) *Prevotella nigrescens;*
y) *Propionibacterium acnes;*
z) *Pseudomonas aeruginosa;*
aa) *Selenomonas noxia;*
bb) *Staphylococcus aureus;*
cc) *Streptococcus constellatus;*
dd) *Streptococcus gordonii;*
ee) *Streptococcus intermedius;*
ff) *Streptococcus mutans;*
gg) *Streptococcus oralis;*
hh) *Streptococcus pneumonia;*
ii) *Streptococcus sanguis;*
kk) *Treponema denticola;*
ll) *Treponema pectinovorum;*
mm) *Treponema socranskii;*
nn) *Veillonella parvula;* and
oo) *Wolinella succinogenes.*

The human histatin proteins have been isolated and sequenced. They have been shown to be a family of twelve related low molecular weight proteins. Comparison of the amino acid sequences of the histatins suggests that histatin 2 and histatins 4–12 may have originated from specific proteolytic cleavage of histatin 1 and histatin 3, respectively. (Oppenheim, F. G. et al. (1988), *J. Biol. Chem.* 263:7472–77; Troxler, R. F. et al. (1990), *J. Dent. Res.* 69(1):2–6). Cloning and sequence analysis of histatin cDNAs further suggest that the histatins are encoded by two homologous genetic loci, whose primary products are histatins 1 and 3. (Sabatini, L. M. et al. (1989), *Biochem. Biophys. Res. Comm.* 160:495–502; Vanderspek, J. C. et al. (1990), *Arch. Oral Biol.* 35(2):137–43).

The amino acid sequences of the anti-fungal and anti-bacterial peptides of this invention represent all or defined portions of the amino acid sequence of peptide 113 (SEQ ID NO: 18). Specific preferred embodiments of this invention are peptide 113 itself (SEQ ID NO: 18), histatin 11 (SEQ ID NO: 11), peptide 129 (SEQ ID NO: 23), peptide 117 (SEQ ID NO: 19), peptide 118 (SEQ ID NO: 20), peptide 119 (SEQ ID NO: 21) and peptide 120 (SEQ ID NO: 22). The amino acid sequences of these preferred peptides are shown in FIGS. 1A–1C. Combinations of two or more of these peptides are also effective as anti-fungal or anti-bacterial compositions and are included as compositions of the invention. The peptides can be obtained from a naturally occurring source of histatin or they can be chemically synthesized or obtained by recombinant DNA techniques as expression products from cellular sources. These peptides can be altered by minor chemical modifications, such as by adding small substituents or by modifying one or more of the covalent bonds within or between the amino acid residues, without significantly diminishing the anti-fungal or anti-bacterial activities of the peptides. Particularly useful modifications are acetylation of the amino terminus of the peptide or amidation of the carboxyl terminus of the peptide. A combination of both modifications is especially useful. Such modifications appear to increase the biological half-life of the peptides before degradation, encapsulation, internalization or excretion occurs.

The peptides described herein were tested in assays designed to measure separately their effectiveness in killing of blastoconidia of *C. albicans* in inhibiting the growth of *P. gingivalis*, in inhibiting hemagglutination caused by *B. forsythus*, and in inhibiting clostripain activity. These assays are indicative of anti-fungal and anti-bacterial activities of the histatin-based peptides of the present invention. When tested in these assays, the histatin-based peptides of this invention were found surprisingly to have superior anti-candidal and anti-bacterial activity, particularly on an equivalent weight basis, when compared with histatin 5 as well as with histatin-based peptides 101–105. These anti-fungal and anti-bacterial activities are surprising in view of their size and truncated peptide form.

The following is a description of the histatin-based peptides, the antifungal activities of the histatin-based peptides as measured in assays for killing of Candida blastoconidia, and the anti-bacterial activities of the histatin-based peptides as measured in assays for inhibition of *P. gingivalis* growth, inhibition of hemagglutination caused by *B. forsythus* and inhibition of clostripain enzyme activity.

Histatin 5 and Histatin-Based Peptides

Histatin 5 and the histatin-based peptides 101, 102, 103, 104, 105, 111, 113, 117, 118, 119, 120 and 129 were chemically synthesized. The amino acid sequences of histatin 5 and the synthesized histatin-based peptides are shown in FIGS. 1A–1C.

Anti-Fungal Activities of Histatin-Based Peptides

*C. albicans* is a dimorphic yeast. It can exist in a yeast or blastoconidial form, which upon germination develops into the hyphal or germinated form. While the germinated form is considered to be more invasive, most of the *C. albicans* isolates harvested from the oral cavities of healthy individuals appear to be in the blastoconidial form. (Arendorf, T. M. et al. (1980), *Arch. Oral Biol.* 25:1–10; Gow, N. A. R. et al. (1987), *Criti. Rev. Microbiol.* 15:73–78; Odds, F. C. (1988), *Candida and Candidosis*, 2nd ed., Bailliere Tindall, London, England). Anti-fungal activity of synthetic histatin 5, histatin-based peptide 113 and peptides based on portions of the amino acid sequences of histatin-based peptide 113 was measured in assays designed to test the effectiveness of the peptides against the blastoconidia form of Candida (Table 1). These assays, which measure killing of blastoconidia of *C. albicans*, are described in Xu et al., which is herein incorporated by reference. (Xu, T. et al. (1991), *Infect. Immun.* 59(8):2549–2554). Peptide 113 was found to be about equipotent with histatin 5, demonstrating its anti-fungal activity despite its size in comparison with histatin 5. Peptides 101–105 demonstrated fungicidal activity comparable to that of histatin 5 and histatin-based peptide 113. Histatin 11, peptides 117–120 and peptide 129 all have demonstrable fungicidal activity even though they are smaller than peptide 113. These latter peptides appear to have the amino acid sequences of peptide 113 (and histatin 5) which are required for anti-fungal activity. The anti-fungal potency of the histatin-based peptide appears to be a function of both the size and the amino acid sequence of the respective peptide. In particular, the anti-fungal potency of human histatins appears to reside in peptide 113 with selected subpeptides of peptide 113 maintaining at least partial anti-fungal activity.

Peptide sequences containing permutations of the amino acid sequences of native histatins and modified peptides can be produced by known methods, such as recombinant DNA techniques and solid-phase synthesis. Cloned DNA encoding the human histatins may be obtained as described by Sabatini et al. or Vanderspek et al., whose teachings are incorporated herein by reference. (Sabatini. L. M. et al. (1989), *Biochem. Biophys. Res. Comm.* 160:495–502; Vanderspek, J. C. et al. (1990), *Arch. Oral Biol.* 35(2):137–43). cDNA encoding the histatin-based peptides can be cloned by recombinant DNA techniques, for instance, by using degenerate oligonucleotides based on the amino acid sequence of the histatin-based peptides as primers for polymerase chain reaction amplification. Alternatively, oligonucleotides encoding histatins or histatin-based peptides can be synthesized chemically using commercially available equipment. They can then be made double-stranded and cloned into vectors for amplification in prokaryotic or eukaryotic host cells.

Histatin-based peptides can be produced in a variety of expression vector/host systems, which are available commercially or can be reproduced according to recombinant DNA and cell culture techniques. The vector/host expression systems can be prokaryotic or eucaryotic, and can include bacterial, yeast, insect, mammalian, and viral expression systems. The construction of expression vectors encoding histatin-based peptides, transfer of the vectors into various host cells, and production of peptides from transformed host cells can be accomplished using genetic engineering techniques, as described in manuals such as *Molecular Cloning* and *Current Protocols in Molecular Biology*, whose teachings are incorporated herein by reference. (Sambrook, J., Fritsch, E. F. and Maniatis, T. (1989), *Molecular Cloning*, 2nd ed., Cold Spring Harbor Laboratory Press; Ausubel, F. M. et al., eds., *Current Protocols in Molecular Biology*, New York; Greene Publishing Associates and Wiley-Interscience)

Modified histatin based peptides can be synthesized chemically, or be produced from cloned DNAs containing mutated nucleotide sequences. Histatin-based peptides encoded by expression vectors may be modified due to post-translational processing in a particular expression vector/host cell system. (See, e.g., Wold, F. (1981), *Ann. Rev. Biochem.* 50:783–814). Histatin-based peptides may also be modified by chemical alteration of amino acid side-chain groups, or by other covalent modification. (See, e.g., Glazer, A. N. et al. (1975), *Chemical Modification of Proteins*, North Holland; Katre, N. V. et al. (1987), *Proc. Natl. Acad. Sci. USA* 84:1487)

Therapeutic Applications

The histatin-based peptides of this invention, representing defined portions of the amino acid sequence of histatin-based peptide 113: peptide 113 itself, histatin 11, peptide 117, peptide 118, peptide 119, peptide 120 and peptide 129, can be used in compositions and methods of treatment for fungal, and in particular, candidal infection, or for bacterial infection. These methods of treatment for fungal or bacterial infection apply to preventive treatment as well. The compositions may contain combinations of histatin-based peptides, in order to obtain maximum activity against all developmental forms of the fungus. The ionic strength, presence of various mono- and divalent ions, and pH of the compositions may be adjusted to obtain maximum anti-fungal or anti-bacterial activity of the histatin-based peptides, as described in Xu et al. (Xu, T. et al. (1991), *Infect. Immun.* 59(8):2549–54). Carriers appropriate for administration of anti-fungal agents to the vagina, the urethra, the oral cavity, the ophthalmic region and skin are known, and described, for instance, in U.S. Pat. No. 4,725,576 (*Fungicidal Polypeptide Compositions Containing L-His and Methods for Use Therefor* by J. J. Pollock and B. J. MacKay, Feb. 16, 1988). Compositions for treatment of systemic infection can be administered by various routes, such as intravenously or subdermally.

Expression vectors encoding the above-mentioned peptides can be used in compositions and methods for anti-fungal or anti-bacterial treatment. Expression vectors may be administered in compositions which introduce genetic material encoding histatin-based peptides into cells of the patients. For example, recombinant expression vectors based on retroviruses or adenovirus vaccines may be used to infect patients.

A method of anti-fungal or anti-bacterial therapy using the above-described expression vectors is bacterial substitution therapy. Bacterial substitution therapy can be used to treat fungal or bacterial infection of areas in the urinary/reproductive and/or gastrointestinal tracts of a patient. The therapy comprises the following: 1) transforming a particular bacterium with DNA comprising an expression vector which encodes a histatin-based peptide described above, thereby producing transformed cells; 2) selecting transformed cells which express the peptide encoded by the expression vector, thereby obtaining transformed cells which express a histatin-based peptide; and 3) administering transformed cells which express a histatin-based peptide in an appropriate carrier to the infected area.

One application of bacterial substitution therapy is treatment of fungal or bacterial infections of the oral cavity. A number of species of the oral bacterial Streptococcus can be used as vehicles for the expression vectors. For example, recombinant *S. lactis* has been used in oral immunization of mice against a heterologous antigen. (Iwaki, M. et al. (1990), *Infect. Immun.* 58(9):2929–34). Other oral bacteria which can be used as vehicles for the expression vectors, plasmids for constructing expression vectors capable of amplification in oral bacterial host cells, transformation methods, and administration of compositions containing oral bacteria to humans have been described. (See, e.g., Kuramitsu, H. K. et al. (1984), *J. General Microbiology* 130:2497–2500; LeBlanc, D. J. et al. (1978), *Proc. Natl. Acad. Sci. USA* 75(7):3484–3487; Macrina, F. L. et al. (1980), *J. Bacteriology* 143(3):1425–1435; Kuramitsu, H. K. et al. (1982), *Infect. Immun.* 36(1):435–436; Svanberg, M. et al. (1984), *Infect. Immun.* 43(3):817–821).

The compositions and methods for treatment of fungal or bacterial infections discussed above are not limited to use in humans, but can have veterinary applications as well.

Furthermore, the above-described compositions and methods for treatment of fungal infection can also be used for treatment of bacterial infections (e.g., of *S. mutans* or *P. gingivalis*) and viral infections (e.g., of herpex simplex virus or human immunodeficiency virus type 1).

Hemagglutination Activity of Bacteria and Histatin Inhibition of this Activity

Even though the association between hemagglutination activity and adherence on host cells in the oral environment is not clear, it is generally accepted that hemagglutination activity is an indicator for colonizing ability of bacteria. Periodontal pathogens must adhere to other bacteria and host cells in order to express their noxious destructive potential upon periodontal tissues. Hemagglutinin is thought to be involved in bacterial colonization. Proteases such as collagenase, sialidase, and trypsin-like protease are involved in the degradation of host tissues, and low-molecular weight toxic products such as butyric and propionic acids which are cytotoxic are produced. In a similar fashion, *B. forsythus* has been shown to possess sialidase and trypsin-like protease. Sialidase has the ability of altering the host response to periodontal microorganisms. For instance, it cleaves sialic acid from erythrocytes and leukocytes which results in removal of these cells from the circulation. It also decreases the ability of IgG to bind complement, decreases collagen production, and stimulates lymphocytes. Trypsin-like protease can cleave a variety of synthetic substrates. It is so called because it can hydrolyse the synthetic substrate benzoyl-DL-arginine-naphylamide (BANA), used for detection of trypsin activity. *P. gingivalis, B. forsythus* and *T. denticola* possess strong BANA hydrolase activity. *B. forsythus* also possesses hemagglutinin(s).

Ability for adherence on erythrocytes is of great importance in the interactions of periodontal pathogens with the host. The close proximity of these bacteria with the host tissues as well as with erythrocytes that bathe the periodontal pocket during progression of the disease, indicates multiple interrelations between these elements. Additionally, periodontal microbes require heme-containing products for their survival and multiplication and this need dictates interactions with cells such as erythrocytes that are rich in these compounds. *P. gingivalis* has been shown to possess both hemagglutinin(s) and hemolysin that provide attachment on erythrocytes and utilization of heme-compounds.

It has been shown (Murakami et al. (1990) *Arch. Oral Biol.* 9:775) that histatin 5 and histatin 8 inhibit hemagglutination of *P. gingivalis* 381. Complete hemagglutination inhibition was reported for histatin 5 at a concentration of 5 nmole/ml. Thus, it appears that histatins and, more importantly, histatin-based peptides can play a role in inhibiting bacterial growth and deleterious activity in the periodontal region.

Clostripain Inhibition by Histatin-Based Peptides

Clostripain is an endopeptidase enzyme synthesized by *Clostridium histolyticum*. This enzyme, with its protein degradative activity, can be inhibited by histatin 5 and by histatin-based peptides (see Table 1). Thus, histatin-based peptides can inhibit bacterial function by inhibiting bacterial enzymes which are essential for the bacterial viability.

EXAMPLE 1 MATERIALS AND METHODS

A. Isolation and Chemical Synthesis of Histatin-Based Peptides

Isolation and amino acid sequence determination of human histatins were performed as described in Oppenheim et al., whose teachings are herein incorporated by reference. (Oppenheim, F. G. et al. (1988), *J. Biol. Chem.* 263(16):7472–7477). Human parotid secretion from healthy adults was stimulated using sour lemon candies, collected with Curby cups in ice-chilled graduated cylinders, pooled, dialyzed and lyophilized. Total protein in human parotid secretion was subjected to fractionation on Bio-Gel P-2 (Bio-Rad Laboratories, Richmond, Calif.) developed in 0.05M ammonium formate buffer, pH 4.0. The protein fraction enriched with histatins was further purified using reversed-phase high-performance liquid chromatography on a $C_{18}$ column. Purified histatins were evaporated to dryness, dissolved in deionixzed water, quantified by amino acid analysis, lyophilized, and stored at -20° C. until use. Histatin-based peptides were synthesized by the solid phase method of Merrifield. (Merrifield, B. (1986) *Science* 232:341–47). Peptides were synthesized by a MilliGen/Bioresearch Sam-Two Peptide Synthesizer using Fmoc L-amino acid kits (Millipore, Bedford, Mass.) and purified on a TSK ODS-i20T $C_{18}$ column (5 μm, 4.6×250 mm) using RP-HPLC (Pharmacia-LKB). The purified peptides were quantified by amino acid analysis on a Beckman System 6300 amino acid analyzer.

B. *C. albicans* Killing (1) *C. albicans* Stock

A well-described strain of *C. albicans* was used in the bioassay. This strain, ATCC 44505, was originally isolated from the human oral cavity. Cultures were stored at 4° C. on Sabouraud dextrose agar plates (Difco Laboratories, Detroit, Mich.) until use. Stationary phase growth cells were obtained following growth at 30° C. for 18 h on Sabouraud dextrose agar plates. Colonies were harvested and suspended in 10 mM potassium phosphate buffer (PPB), pH 7.4.

To initiate log phase growth, an aliquot of stock *C. albicans* was suspended in Sabouraud dextrose broth (Difco) and incubated at 30° C. in a shaking water bath. The growth phase was determined by taking aliquots of the culture at one hour intervals to monitor the optical density (O.D.) at 560 nm. Early log phase was obtained at 4 to 6 h, indicated by an O.D. of about 0.6. Log phase cells were harvested and utilized in the blastoconidia killing assay in a manner identical to that described for stationary phase cells. A final concentration of $10^5$ cells/ml (either stationary or log phase fungus) was used in all assays.

(2) Suspension Buffers

The standard suspension buffer utilized in the blastospore killing assay was 0.01M PPB, pH 7.4. An alternate suspension buffer, N-2-hydroxyethylpiperazine-N'-2-ethanesulfonic acids (HEPES; Sigma Chemical Co., St. Louis, Mo.), pH 7.4, can also be utilized.

(3) Bioassays

The following assay was used to evaluate the effects of histatins on the killing of blastoconidia of *C. albicans*.

a. For the killing of blastoconidia assay, 50 μl aliquots of cells ($2\times10^5$ cells/ml) diluted in suspension buffer were allowed to attach to a polystyrene 96-well micro-titer plate (COSTAR, Cambridge, Mass.) for 15 min at room temperature, and then incubated with an equal volume of a histatin or histatin peptide in suspension buffer for 1 h at 37° C. Controls were carried out in the absence of the histatin or histatin peptide. After incubation, wells were washed three times by centrifugation at 1,000 xg for 5 min and covered with aliquots of molten Sabouraud dextrose broth (Difco) containing 2% agarose (Sigma) at 45° C. The plate was then incubated at 30° C. for 8 h. Under such conditions, live cells will divide and begin to form colonies, while dead cells will remain as single cells. To determine the percentage of blastoconidia killed, a total of 100 single cells and/or colonies were counted under a Nikon inverted microscope at 400× magnification and the extent of killing was calculated using the formula: [1—(number of colonies in treated sample)/(number of colonies in control)]×100%.

(4) Statistical Analysis

Data were obtained by calculating the mean and standard deviation from triplicate assays. From the dose response relationship, doses effecting a 50% killing ($LD_{50}$).

C. BACTERIAL GROWTH INHIBITION ASSAY (1) Bacterial Strains and Culture Conditions The bacteria used in this investigation, *Porphyromonas gingivalis* strain A7A1-28, is a typical key pathogenic organism associated with destructive periodontal diseases. The bacteria were multiply subcultured in Enriched Todd Hewitt broth (ETHB, Difco Lab., Detroit, Mich.). Microorganisms were stored in the same broths containing 20% and 50% glycerol, at −20° C. and −70° C., respectively. These served as stock cultures from which all preparations originated.

Working stock cultures were maintained by weekly transfer to Brain Heart Infusion Anaerobic Sheep Blood Agar plates (BHIA, Becton Dickinson and Co., Cockeysville, Md.), and Trypticase Soy Anaerobic Sheep Blood Agar plates (TSA, Becton Dickinson and Co., Cockeysville, Md.). Plates were incubated for 3 to 4 days under strictly anaerobic conditions. For the bacteriostatic assay, bacteria were collected from plates, inoculated into the aforementioned broth and grown at 37° C., under strictly anaerobic conditions for 24 to 48 hours.

(2) Microdilution Bacteriostatic Assay

A modification of the typical microdilution assay (Rotilie et al., 1975) for the determination of minimal inhibitory concentration (MIC) of antimicrobial agents was utilized to investigate the bacteriostatic activity of the peptides. A standardized bacterial inoculum was exposed to serially diluted antimicrobial peptides in an enriched broth medium that was suitable for the growth of anaerobic bacteria. The test was adapted for use in the 96-well microtiter plates. Results with the microdilution method have been shown to be comparable to the other known techniques for antimicrobial susceptibility such as the dilution method, the agar dilution method, and the broth-disk elution method (Rosenblatt et al., 1979). In the typical assay, the microtiter plate was observed at multiple time points after incubation for visible growth. The modification introduced here was based on the spectrophotometric reading of the microtiter plate after incubation.

Microorganisms from cultures maintained in the aforementioned plates were inoculated into 5 ml of the above-mentioned broths and cultured overnight at 37° C. under strictly anaerobic conditions with continuous agitation on a minishaker (IKA-Labortechnik, Staufen i. Br., Germany). The bacteria were grown until reaching the late log phase and were then suspended in the same broths to an optical density (O.D.) of 0.1 at 560 nm. The peptides were diluted in 0.01M phosphate buffered saline (PBS), pH 7. Forty µl aliquots of peptide dilutions were added in each well of a U-bottom microtiter plate (Costar, Cambridge, Mass.) to give final concentrations of 2000, 1000, 500 and 250 µM. Twenty µl of bacterial inoculum was added to all the wells. Finally, 100 µl of the suitable broth were added to each well. The optical density of the wells of the microtiter plate was determined using a microplate reader set at 550 nm and the plate was then incubated under strictly anaerobic conditions for 24 hours. Controls were made by replacing the peptide dilutions with PBS alone. After the incubation, the mixtures in each well were mixed manually to resuspend sedimented bacteria and the plate was read again. The experiments were conducted twice every time. The biologic activity was calculated according to the formula:

$$100-[[(Fin\ ODexp-In\ ODexp)/(Fin\ ODctr-In\ ODctr)]\times 100]$$

where:

Fin ODexp is the OD of the final experimental group;
In ODexp is the OD of the initial experimental group;
Fin ODctr is the OD of the final control group; and
In ODctr is the OD of the initial control group.

In addition, the % increase in time to reach mid-log phase growth was calculated.

The data presentation represent the means (±SEM) of at least 2 separate experiments.

D. INHIBITION OF HEMAGGLUTINATION ASSAYS (1) Strains and Growth Conditions for Hemagglutination Assays The *P. gingivalis* strain of Section C.(1) was also used for the hemagglutination assays. The bacterial growth and culture conditions were also the same as those described in Section C.(1).

(2) Hemagglutination Assay

A classic assay was utilized to determine the hemagglutination potential of the *P. gingivalis* strain. Microorganisms were inoculated into BFB broth and cultured overnight, for approximately 24 hours at 37° C. under strictly anaerobic conditions with continuous agitation on a minishaker (IKA-Labortechnik, Staufen i. Br., Germany). The bacteria were harvested by centrifugatin at 3,000 r.p.m. for 20 min, at 4° C., washed twice in 0.01M phosphate buffered saline (PBS), pH 7.4, and suspended in the same buffer to an optical density of 1.0 at 550 nm. Erythrocytes were obtained from a young male with O-type blood, since no difference in hemagglutination was observed in preliminary experiments with different ABO blood groups. One ml of blood was drawn each time, washed twice in PBS at 1,000 r.p.m. for 10 min at 4° C. and suspended in the same buffer at a 2% (v/v) final concentration. Fifty µl of the bacterial suspension were serially diluted in PBS (two-fold steps) in a 96-well U-bottom microplate (Costar, Cambridge, Mass.). Fifty µl of the erythrocyte suspension were added to each well. Controls without bacteria or erythrocytes were included. The microplate was slightly shaken and incubated at room temperature for 2 hours. Visible examination on a white background was used to determine hemagglutination. The amount of hemagglutination was rated as none (−), moderate (±), or strong (+). Erythrocytes in control wells with PBS precipitated to the center of the well, whereas erythrocyte-bacteria aggregates precipitated at the periphery of the bottom. The hemagglutination titer was expressed as the reciprocal of the highest dilution of the bacterial suspension providing visible hemagglutination.

(3) Histatin Peptide Inhibition of Hemagglutination Assay

Preparation of erythrocyte and bacterial suspensions were the same as for the hemagglutination assay. Fifty µl of histatin peptide solutions were diluted in PBS in a U-bottom microplate, at various two-fold concentrations with 600 nmole/ml being the highest. The bacterial concentration utilized was normally twice the minimal concentration which gave strong hemagglutination. Equal volumes of the bacterial suspension were poured into the wells containing the histatin peptides. Finally, 50 µl of erythrocyte suspension were added in each well. The microplate was slightly shaken and incubated at room temperature for 2 hours. Controls were made by replacement of the peptide dilutions with PBS only. The experiments were conducted at least twice. The lowest histatin peptide concentration without hemagglutination (complete inhibition) was determined upon visual examination. The highest final histatin peptide concentration utilized was 100 nmole/ml.

E. CLOSTRIPAIN ASSAYS

Clostripain from *Clostridium histolyticum* (Sigma Chemical Corp., St. Louis, Mo.) was dissolved in deionized water to a concentration of 1 mg/mL (300 units/mg) and activated with the addition of 10 mmol/L DTT. To measure its hydrolytic activity, clostripain (6 units) was added to 50 nmol/L Hepes buffer, pH 7.5, containing 80 µmol/L BAPNA (benzoyl-arginine-p-nitroanilide), together with 5.6 µmol/L of histatin peptide inhibitor. As controls, assays were performed in the absence of any histatin peptide inhibitor. The activity was monitored continuously at 405 nm using a Molecular Devices $V_{Max}$ microtitre plate reader. The activities were determined from the maximum rates of substrate hydrolysis. Assays were done in duplicate, and the means normalized to the controls.

EXAMPLE 2. EFFECTS OF HISTATIN PEPTIDES ON FUNGAL OR BACTERIAL VIABILITY

Figure 3:
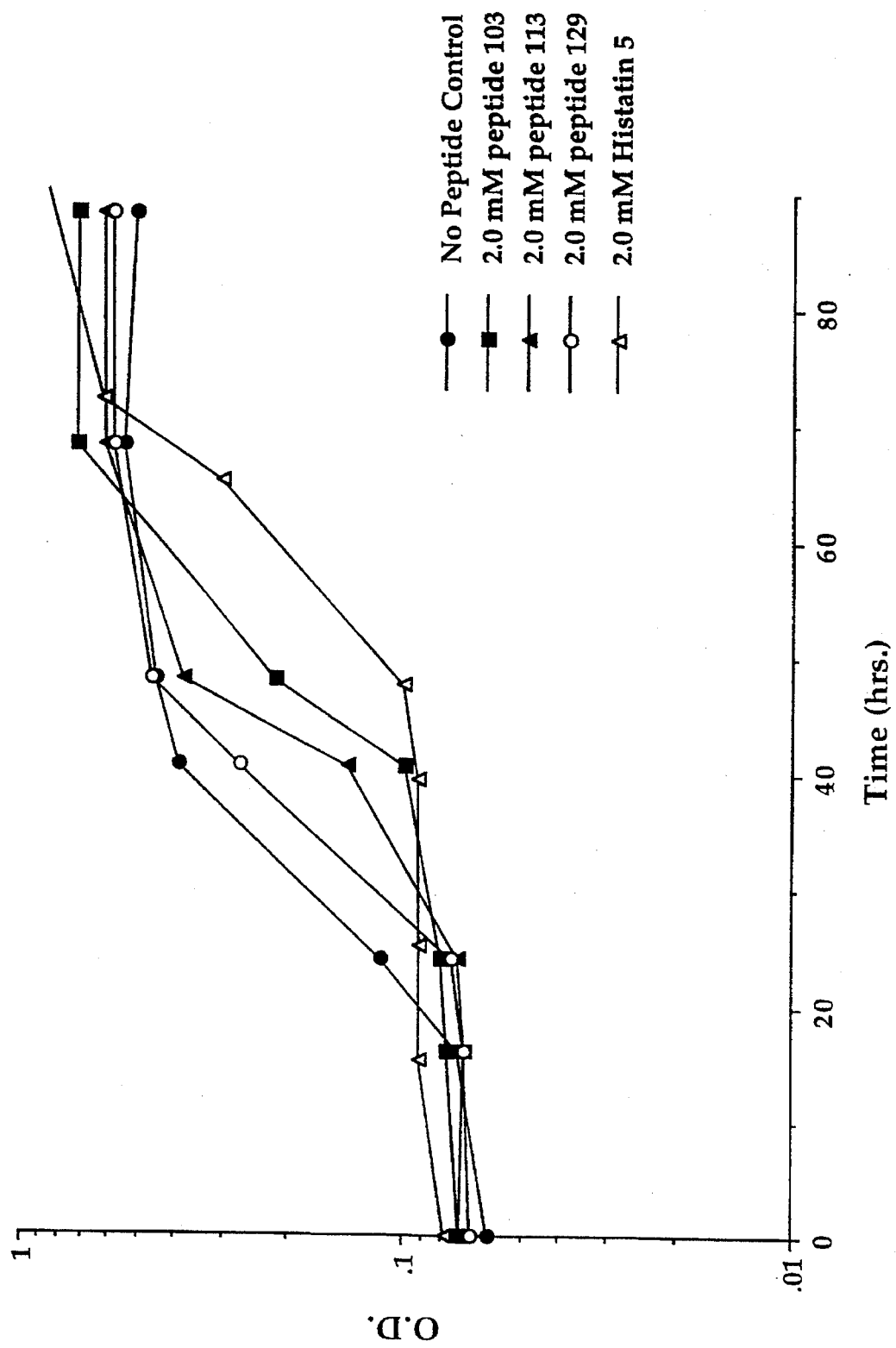
FIG. 3 is a graph that shows the amount of growth inhibition of *P. gingivalis* as a function of time for histatin 5, peptide 103, peptide 113 and peptide 129, as well as when no histatin-based peptide is present.
Figure 4:
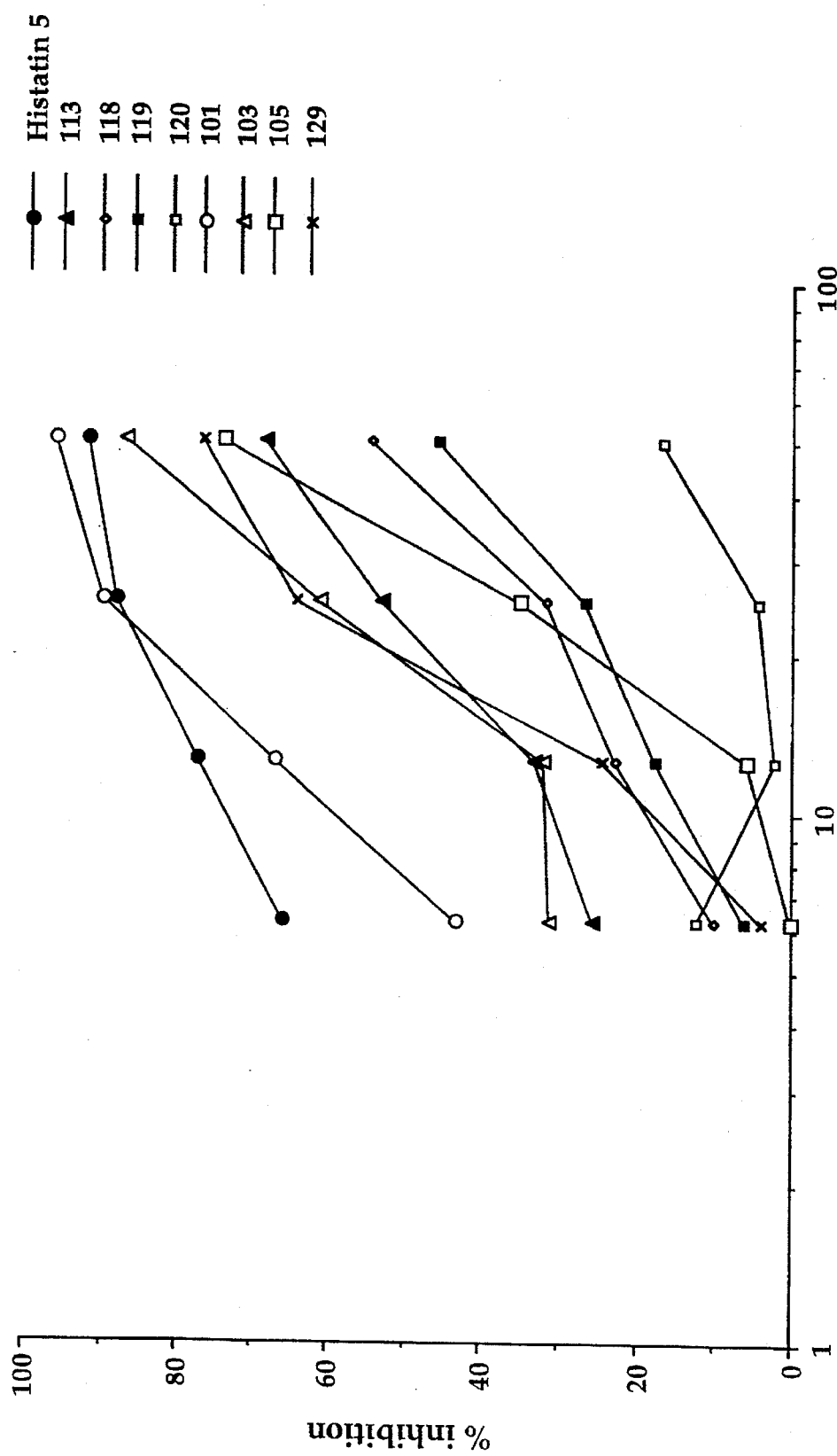
FIG. 4 is a graph that shows the % inhibition of clostripain activity as a function of the concentration of histatin 5, peptide 101, peptide 103, peptide 105, peptide 118, peptide 119, peptide 120 and peptide 129.

FIGS. 2–4 and Table 1 summarize the results of the fungal killing, bacterial growth inhibition, bacteria mediated hemagglutination inhibition and bacterial enzyme (clostripain) inhibition effects of histatin 5 and several tested histatin peptides. For comparison purposes, the anti-fungal and anti-bacterial effects of histatin 11 and the histatin-based peptides were assessed with synthesized histatin 5 as a standard. Histatin 11 and histatin-based peptides 113, 117, 118, 119, 120 and 129 have *C. albicans* blastoconidia killing, *P. gingivalis* growth inhibition, bacteria mediated hemagglutination inhibition and clostripain inhibition effects. These antimicrobial effects are similar to those observed for histatin 5 and for histatin-based peptides 101–105. Although expected variations exist in anti-fungal and anti-bacterial effects between the tested peptides, the antimicrobial effects of the histatin-based peptides are comparable to those of histatin 5. These results demonstrate that these histatin-based peptides are efficacious as anti-fungal or anti-bacterial agents. In particular, these results demonstrate that histatin-based peptide 113 and its subpeptides histatin 11, histatin-based peptides 117, 118, 119, 120 and 129 are more efficacious on the basis of molecular weight or amino acid sequence length than histatin 5. The anti-fungal and anti-bacterial activity of the histatins appears to be concentrated in the amino acid sequence of histatin-based peptide 113.

TABLE 1

SUMMARY OF HISTATIN PEPTIDE SEQUENCES AND BIOLOGICAL ACTIVITY TESTING

| Histatin Peptide | MW | C. albicans | P. gingivalis | Hemagglut | Clostripain |
|---|---|---|---|---|---|
| SynHis5 | 3037 | 3.0 µM | 88.7% | 3.12 µM | <6.2 µM |
| 101 | 2025 | 3.5 | | 1.56 | 7.5 |
| 102 | | 10 | +++ | | |
| 103 | 2613 | 4.5 | 56.6 | 1.56 | 19 |
| 104 | 2055 | NA | | | |
| 105 | 2978 | 5.0 | +++ | 6.25 | 3.3 |
| His 11 | 1080 | + | | 100 | NA |
| 113 | 1563 | 5.8 | 34.95 | 25 | 25 |
| 117 | 1492 | ++++ | | | |
| 118 | 1426 | ++++ | | 6.25 | 45 |
| 119 | 1279 | ++ | | 25 | >50 |
| 120 | 1151 | ++ | | 50 | >50 |
| 129 | | 27 | 15.4 | 50 | 19 |

Key:
C. albicans: Results expressed as $LD_{50}$ (µM) for % killing or % killing at 50 µM dose (see below for scoring).
P. gingivalis: Results expressed as % increase in time to reach mid log-phase growth (0.2 OD) for the 2 mM dose or % inhibition at 500 µM dose (see below for scoring).
Hemagglutination: Results expressed as lowest dose (µM) at which hemagglutination was observed using P. Gingivalis.
Clostripain: Results expressed as $IC_{50}$ (µM) for inhibition of Clostripain.
Scoring: The highest response seen was used in the scoring.
++++ 80–100%
+++ 50–80%
++ 20–50%
+ <20%
NA Not Active

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A composition for treating a fungal or bacterial infection comprising a substantially pure peptide having an amino acid sequence, of at least 8 amino acids, selected from the amino acid sequence of peptide 113 as set forth in SEQ ID NO: 18.

2. A composition of claim 1 wherein said substantially pure peptide is selected from the group consisting of:
   a) the amino acid sequence of peptide 113 as set forth in SEQ ID NO: 18;
   b) the amino acid sequence of histatin 11 as set forth in SEQ ID NO: 11;
   c) the amino acid sequence of peptide 129 as set forth in SEQ ID NO: 23;
   d) the amino acid sequence of peptide 117 as set forth in SEQ ID NO: 19;
   e) the amino acid sequence of peptide 118 as set forth in SEQ ID NO: 20;
   f) the amino acid sequence of peptide 119 as set forth in SEQ ID NO: 21;
   g) the amino acid sequence of peptide 120 as set forth in SEQ ID NO: 22; and
   h) combinations of two or more of the above.

3. Substantially pure peptide having an amino acid sequence, of at least nine amino acids, selected from the amino acid sequence of peptide 113 as set forth in SEQ ID NO: 18.

4. Substantially pure peptide of claim 3 selected from the group consisting of:
   a) the amino acid sequence of peptide 113 as set forth in SEQ ID NO: 18;
   b) the amino acid sequence of peptide 129 as set forth in SEQ ID NO: 23;
   c) the amino acid sequence of peptide 117 as set forth in SEQ ID NO: 19;
   d) the amino acid sequence of peptide 118 as set forth in SEQ ID NO: 20;
   e) the amino acid sequence of peptide 119 as set forth in SEQ ID NO: 21; and
   f) the amino acid sequence of peptide 120 as set forth in SEQ ID NO: 22.

5. A method for treating a fungal or bacterial infection in an individual comprising administering to said individual a therapeutically effective amount of at least one peptide having an amino acid sequence, of at least 8 amino acids, selected from the amino acid sequence of peptide 113 as set forth in SEQ ID NO: 18.

6. A method for treating a fungal or bacterial infection of claim 5 wherein said peptide is selected from the group consisting of:
   a) the amino acid sequence of peptide 113 as set forth in SEQ ID NO: 18;
   b) the amino acid sequence of histatin 11 as set forth in SEQ ID NO: 11;
   c) the amino acid sequence of peptide 129 as set forth in SEQ ID NO: 23;
   d) the amino acid sequence of peptide 117 as set forth in SEQ ID NO: 19;
   e) the amino acid sequence of peptide 118 as set forth in SEQ ID NO: 20;
   f) the amino acid sequence of peptide 119 as set forth in SEQ ID NO: 21; and
   g) the amino acid sequence of peptide 120 as set forth in SEQ ID NO: 22.

7. A method for treating a fungal or bacterial infection of claim 5 wherein said fungal or bacterial infection is selected from the group consisting of:
   a) an infection of the oral cavity;
   b) an infection of the vagina;
   c) an infection of the urethra;
   d) an infection of the skin;
   e) an ophthalmic infection; and
   f) a systemic infection.

8. A method for treating a fungal or bacterial infection of claim 7 wherein the fungus or bacterium is selected from the group consisting of:
   a) *Candida albicans;*
   b) *Actinomyces actinomycetemcomitans;*
   c) *Actinomyces viscosus;*
   d) *Bacteroides forsythus;*
   e) *Bacteriodes fragilis;*
   f) *Bacteriodes gracilis;*
   g) *Bacteriodes ureolyticus;*
   h) *Campylobacter concisus;*
   i) *Campylobacter rectus;*
   j) *Campylobacter showae;*
   k) *Campylobacter sputorum;*
   l) *Capnocytophaga gingivalis;*
   m) *Capnocytophaga ochracea;*
   n) *Capnocytophaga sputigena;*
   o) *Clostridium histolyticum;*
   p) *Eikenella corrodens;*
   q) *Eubacterium nodatum;*
   r) *Fusobacterium nucleatum;*
   s) *Fusobacterium periodonticum;*
   t) *Peptostreptococcus micros;*
   u) *Porphyromonas endodontalis;*
   v) *Porphyromonas gingivalis;*
   w) *Prevotella intermedia;*
   x) *Prevotella nigrescens;*
   y) *Propionibacterium acnes;*
   z) *Pseudomonas aeruginosa;*
   aa) *Selenomonas noxia;*
   bb) *Staphylococcus aureus;*
   cc) *Streptococcus constellatus;*
   dd) *Streptococcus gordonii;* ee) *Streptococcus intermedius;*
ff) *Streptococcus mutans;*
gg) *Streptococcus oralis;*
hh) *Streptococcus pneumonia;*
ii) *Streptococcus sanguis;*
kk) *Treponema denticola;*
ll) *Treponema pectinovorum;*
mm) *Treponema socranskii;*
nn) *Veillonella parvula;* and
oo) *Wolinella succinogenes.*

* * * * *